(12) United States Patent
Liu et al.

(10) Patent No.: US 9,039,989 B2
(45) Date of Patent: May 26, 2015

(54) DISINFECTION CAP FOR DISINFECTING A MALE LUER END OF AN INFUSION THERAPY DEVICE

(71) Applicant: Becton, Dickinson and Company, Franklin Lakes, NJ (US)

(72) Inventors: Huibin Liu, West Jordan, UT (US); Minh Quang Hoang, Sandy, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 145 days.

(21) Appl. No.: 13/766,556

(22) Filed: Feb. 13, 2013

(65) Prior Publication Data
US 2014/0227144 A1 Aug. 14, 2014

(51) Int. Cl.
| | |
|---|---|
| *A61L 2/00* | (2006.01) |
| *A61L 2/16* | (2006.01) |
| *A61M 39/16* | (2006.01) |
| *A61M 39/20* | (2006.01) |
| *A61M 39/00* | (2006.01) |

(52) U.S. Cl.
CPC *A61L 2/16* (2013.01); *A61M 39/16* (2013.01); *A61M 39/162* (2013.01); *A61M 39/20* (2013.01); *A61M 2039/0036* (2013.01)

(58) Field of Classification Search
CPC ......... A61L 2/16; A61M 39/16; A61M 39/20
USPC ....................................................... 422/300
See application file for complete search history.

(56) References Cited

U.S. PATENT DOCUMENTS

| | | |
|---|---|---|
| 2,961,682 A | 11/1960 | Wurmbock et al. |
| 4,280,632 A | 7/1981 | Yuhara |
| 4,282,891 A | 8/1981 | Duceppe |
| 4,354,490 A | 10/1982 | Rogers |
| 4,417,890 A | 11/1983 | Dennehey et al. |
| 4,432,764 A | 2/1984 | Lopez |
| 4,440,207 A | 4/1984 | Genatempo et al. |
| 4,444,310 A | 4/1984 | Odell |
| 4,584,192 A | 4/1986 | Dell et al. |
| 4,624,664 A | 11/1986 | Peluso et al. |
| 4,626,664 A | 12/1986 | Grise |
| 4,655,762 A | 4/1987 | Rogers |

(Continued)

FOREIGN PATENT DOCUMENTS

| | | |
|---|---|---|
| EP | 1 649 890 A1 | 4/2006 |
| WO | 87/00441 | 1/1987 |

(Continued)

*Primary Examiner* — Kevin Joyner
(74) *Attorney, Agent, or Firm* — Jeanne Lukasavage; Craig Metcalf; Kirton McConkie

(57) ABSTRACT

The present invention extends to a disinfection cap for disinfecting a male luer end of an infusion therapy device. The disinfection cap can include an internal reservoir containing an antimicrobial or saline solution which is sealed with a flexible septum to prevent the solution from evaporating. The septum can include one or more slits or pierceable seams that allow a male luer end of an infusion therapy device to be inserted through the septum and into the solution. While the male luer is inserted through the septum, the solution contacts both the inner and outer surfaces of the male luer. Because the septum reduces evaporation of the solution and prevents the solution from leaking out of the cap, the solution remains in contact with the male luer for a longer duration then when typical disinfection caps are used thereby increasing the effectiveness of the disinfectant.

20 Claims, 14 Drawing Sheets

(56) References Cited

U.S. PATENT DOCUMENTS

| | | | |
|---|---|---|---|
| 4,671,306 A | 6/1987 | Spector | |
| 4,716,032 A | 12/1987 | Westfall et al. | |
| 4,778,447 A | 10/1988 | Velde et al. | |
| 4,915,934 A | 4/1990 | Tomlinson | |
| 4,925,668 A | 5/1990 | Khan et al. | |
| 4,989,733 A | 2/1991 | Patry | |
| 4,991,629 A | 2/1991 | Ernesto et al. | |
| 5,023,082 A | 6/1991 | Friedman et al. | |
| 5,195,957 A | 3/1993 | Tollini | |
| 5,242,425 A | 9/1993 | White et al. | |
| 5,334,388 A | 8/1994 | Hoang et al. | |
| 5,335,373 A | 8/1994 | Dresdner, Jr. et al. | |
| 5,512,199 A | 4/1996 | Khan et al. | |
| 5,547,662 A | 8/1996 | Khan et al. | |
| 5,554,106 A | 9/1996 | Layman-Spillar et al. | |
| 5,554,135 A | 9/1996 | Menyhay | |
| 5,569,207 A | 10/1996 | Gisselberg et al. | |
| 5,616,338 A | 4/1997 | Fox, Jr. et al. | |
| 5,620,424 A | 4/1997 | Abramson | |
| 5,639,310 A | 6/1997 | Giampaolo, Jr. | |
| 5,641,464 A | 6/1997 | Briggs, III et al. | |
| 5,686,096 A | 11/1997 | Khan et al. | |
| 5,694,978 A | 12/1997 | Heilmann et al. | |
| 5,706,944 A | 1/1998 | Hoang et al. | |
| 5,722,537 A | 3/1998 | Sigler | |
| 5,792,120 A | 8/1998 | Menyhay | |
| 5,817,344 A | 10/1998 | Hoang et al. | |
| 5,861,440 A | 1/1999 | Gohla et al. | |
| 5,954,957 A | 9/1999 | Chin-Loy et al. | |
| 6,045,539 A | 4/2000 | Menyhay | |
| 6,051,609 A | 4/2000 | Yu et al. | |
| 6,116,468 A | 9/2000 | Nilson | |
| 6,117,114 A | 9/2000 | Paradis | |
| 6,227,391 B1 | 5/2001 | King | |
| 6,337,357 B1 | 1/2002 | Fukunishi et al. | |
| 6,413,539 B1 | 7/2002 | Shalaby | |
| 6,488,942 B1 | 12/2002 | Ingemann | |
| RE38,145 E | 6/2003 | Lynn | |
| 6,708,363 B2 | 3/2004 | Larsen | |
| 6,846,846 B2 | 1/2005 | Modak et al. | |
| 6,861,060 B1 | 3/2005 | Luriya et al. | |
| 6,911,025 B2 | 6/2005 | Miyahara | |
| 6,994,315 B2 | 2/2006 | Ryan et al. | |
| 7,083,605 B2 | 8/2006 | Miyahara | |
| 7,198,611 B2 | 4/2007 | Connell et al. | |
| 7,198,800 B1 | 4/2007 | Ko | |
| 7,268,165 B2 | 9/2007 | Greten et al. | |
| 7,282,186 B2 | 10/2007 | Lake, Jr. et al. | |
| 7,452,349 B2 | 11/2008 | Miyahara | |
| 7,682,561 B2 | 3/2010 | Davis et al. | |
| 7,704,935 B1 | 4/2010 | Davis et al. | |
| 7,828,186 B2 | 11/2010 | Wales | |
| 7,922,701 B2 | 4/2011 | Buchman | |
| 8,065,773 B2 | 11/2011 | Vaillancourt et al. | |
| 8,113,731 B2 | 2/2012 | Cable, Jr. et al. | |
| 8,162,899 B2 | 4/2012 | Tennican | |
| 8,167,847 B2 | 5/2012 | Anderson et al. | |
| 8,491,546 B2 | 7/2013 | Hoang et al. | |
| 2001/0016589 A1 | 8/2001 | Modak et al. | |
| 2002/0144705 A1 | 10/2002 | Brattesani et al. | |
| 2003/0072781 A1 | 4/2003 | Pelerin | |
| 2003/0162839 A1 | 8/2003 | Symington et al. | |
| 2004/0004019 A1 | 1/2004 | Busch | |
| 2004/0039349 A1 | 2/2004 | Modak et al. | |
| 2005/0124970 A1 | 6/2005 | Kunin et al. | |
| 2005/0147524 A1 | 7/2005 | Bousquet | |
| 2005/0147525 A1 | 7/2005 | Bousquet | |
| 2006/0030827 A1 | 2/2006 | Raulerson et al. | |
| 2006/0165751 A1 | 7/2006 | Chudzik et al. | |
| 2006/0239954 A1 | 10/2006 | Sancho | |
| 2007/0112333 A1 | 5/2007 | Hoang et al. | |
| 2007/0202177 A1 | 8/2007 | Hoang | |
| 2007/0225660 A1 | 9/2007 | Lynn | |
| 2007/0282280 A1* | 12/2007 | Tennican | 604/246 |
| 2008/0027399 A1 | 1/2008 | Harding et al. | |
| 2008/0033371 A1 | 2/2008 | Updegraff et al. | |
| 2008/0075761 A1 | 3/2008 | Modak et al. | |
| 2008/0095680 A1 | 4/2008 | Steffens et al. | |
| 2008/0147047 A1 | 6/2008 | Davis et al. | |
| 2008/0177250 A1 | 7/2008 | Howlett et al. | |
| 2008/0182921 A1 | 7/2008 | Suh et al. | |
| 2009/0008393 A1 | 1/2009 | Howlett et al. | |
| 2009/0028750 A1 | 1/2009 | Ryan | |
| 2009/0062766 A1 | 3/2009 | Howlett et al. | |
| 2009/0149819 A1 | 6/2009 | Chelak | |
| 2010/0000040 A1 | 1/2010 | Shaw et al. | |
| 2010/0047123 A1 | 2/2010 | Solomon et al. | |
| 2010/0049170 A1 | 2/2010 | Solomon et al. | |
| 2010/0050351 A1 | 3/2010 | Colantonio et al. | |
| 2010/0172794 A1* | 7/2010 | Ferlic et al. | 422/28 |
| 2010/0292673 A1 | 11/2010 | Korogi et al. | |
| 2011/0150958 A1 | 6/2011 | Davis et al. | |
| 2011/0290799 A1 | 12/2011 | Anderson et al. | |
| 2012/0016318 A1 | 1/2012 | Hoang et al. | |
| 2012/0039765 A1 | 2/2012 | Solomon et al. | |
| 2012/0216360 A1 | 8/2012 | Rogers et al. | |
| 2012/0283693 A1 | 11/2012 | Anderson et al. | |

FOREIGN PATENT DOCUMENTS

| | | |
|---|---|---|
| WO | 99/29173 | 6/1999 |
| WO | 2006/019782 A2 | 2/2006 |
| WO | 2007/137056 A2 | 11/2007 |
| WO | 2008/157092 A1 | 12/2008 |
| WO | 2010/039171 A1 | 4/2010 |
| WO | 2010/143693 A1 | 12/2010 |

* cited by examiner

DISINFECTION CAP FOR DISINFECTING A MALE LUER END OF AN INFUSION THERAPY DEVICE

BACKGROUND OF THE INVENTION

Infusion therapy generally involves the administration of a medication intravenously. When performing a typical infusion therapy, one or more infusion therapy device (e.g. tubing sets) are used. Oftentimes, during infusion therapy, the end of the tubing set is left exposed to non-sterile surfaces such as when a syringe is removed from a male luer end of the tubing set. For example, when the end of the tubing set is exposed, the patient or nurse may touch the end, or the end may come in contact with non-sterile bedding, table, or floor surfaces.

Although it is required to clean the hub or needless connector end of the tubing set, it is not required to clean the other end which is typically a male luer. Disinfection caps are increasingly being used to disinfect the ends of infusion therapy devices such as needleless connectors, IV sets, or short extension tubing. Such caps generally include foam soaked with alcohol which contacts surfaces of the port when the cap is connected to the port. Various problems exist when using these caps. For example, the alcohol soaked foam only contacts exterior surfaces of the access port. Also, once a cap is placed on a port, the alcohol in the cap evaporates quickly.

BRIEF SUMMARY OF THE INVENTION

The present invention extends to a disinfection cap for disinfecting a male luer end of an infusion therapy device. The disinfection cap can include an internal reservoir containing an antimicrobial or saline solution which is sealed with a flexible septum to prevent the solution from evaporating. The septum can include one or more slits or pierceable seams that allow a male luer end of an infusion therapy device to be inserted through the septum and into the solution. While the male luer is inserted through the septum, the solution contacts both the inner and outer surfaces of the male luer. Because the septum reduces evaporation of the solution and prevents the solution from leaking out of the cap, the solution remains in contact with the male luer for a longer duration then when typical disinfection caps are used thereby increasing the effectiveness of the disinfectant.

In one embodiment, a disinfection cap comprises an outer support structure, an inner support structure, and a septum. The inner support structure has an inside diameter that is greater than the outside diameter of a male luer, and contains a solution for disinfecting the inner and outer surfaces of the male luer when inserted into the inner support structure. The septum is attached to a top surface of the inner support structure thereby forming a seal for maintaining the solution within the inner support structure. The septum is pierceable to allow a male luer to be inserted through the septum into the inner support structure.

In another embodiment, a disinfection cap comprises an outer support structure, an inner support structure, a frame, and a septum. The inner support structure has an inside diameter that is greater than the outside diameter of a male luer, and contains a solution for disinfecting the inner and outer surfaces of the male luer when inserted into the inner support structure. The frame is configured to be inserted into the cap. The septum attaches to the frame such that when the frame is inserted into the cap, the septum is secured to or against a top surface of the inner support structure thereby forming a seal for maintaining the solution within the inner support structure. The septum is pierceable to allow a male luer to be inserted through the septum into the inner support structure.

In another embodiment, a disinfection cap comprises an outer support structure, an inner support structure, and a silicone septum. The inner support structure has an inside diameter that is greater than the outside diameter of a male luer, and contains a solution for disinfecting the inner and outer surfaces of the male luer when inserted into the inner support structure. The silicone septum is secured to or against the inner support structure thereby forming a seal for maintaining the solution within the inner support structure. The silicone septum includes one or more slits that allow a male luer to be inserted through the septum into the inner support structure. The slits are configured such that when the male luer is inserted through the septum, the septum is secured around the outer surface of the male luer to inhibit the flow of solution out of the inner support structure.

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE INVENTION

Figure 1A:
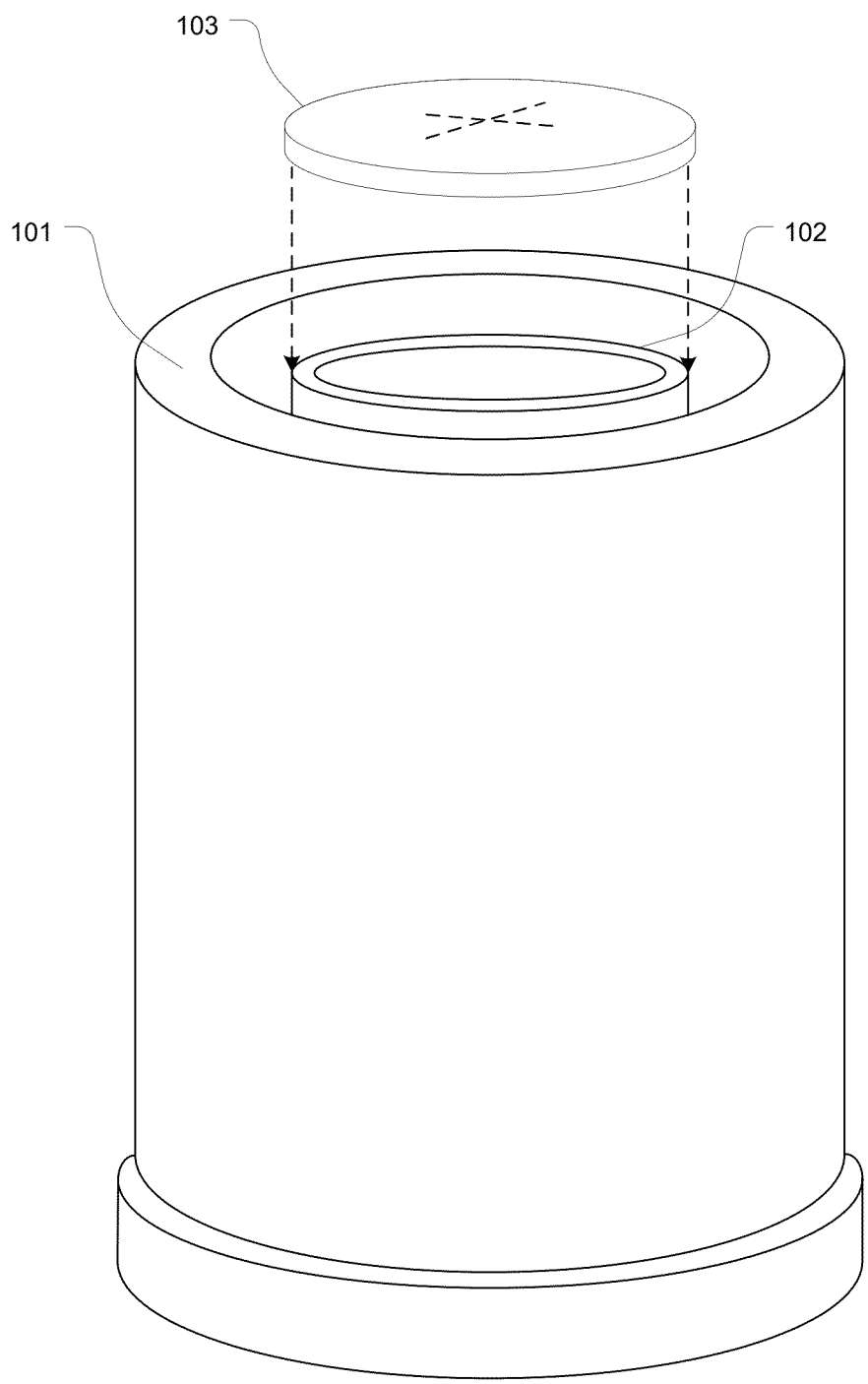
FIG. 1A illustrates a perspective view of an exemplary disinfection cap according to one or more embodiments of the invention.

The present invention extends to a disinfection cap for disinfecting a male luer end of an infusion therapy device. The disinfection cap can include an internal reservoir containing an antimicrobial or saline solution which is sealed with a flexible septum to prevent the solution from evaporating. The septum can include one or more slits or pierceable seams that allow a male luer end of an infusion therapy device to be inserted through the septum and into the solution. While the male luer is inserted through the septum, the solution contacts both the inner and outer surfaces of the male luer. Because the septum reduces evaporation of the solution and prevents the solution from leaking out of the cap, the solution remains in contact with the male luer for a longer duration then when typical disinfection caps are used thereby increasing the effectiveness of the disinfectant.

In one embodiment, a disinfection cap comprises an outer support structure, an inner support structure, and a septum. The inner support structure has an inside diameter that is greater than the outside diameter of a male luer, and contains a solution for disinfecting the inner and outer surfaces of the male luer when inserted into the inner support structure. The septum is attached to a top surface of the inner support structure thereby forming a seal for maintaining the solution within the inner support structure. The septum is pierceable to allow a male luer to be inserted through the septum into the inner support structure.

In another embodiment, a disinfection cap comprises an outer support structure, an inner support structure, a frame, and a septum. The inner support structure has an inside diameter that is greater than the outside diameter of a male luer, and contains a solution for disinfecting the inner and outer surfaces of the male luer when inserted into the inner support structure. The frame is configured to be inserted into the cap. The septum attaches to the frame such that when the frame is inserted into the cap, the septum is secured to or against a top surface of the inner support structure thereby forming a seal for maintaining the solution within the inner support structure. The septum is pierceable to allow a male luer to be inserted through the septum into the inner support structure.

In another embodiment, a disinfection cap comprises an outer support structure, an inner support structure, and a silicone septum. The inner support structure has an inside diameter that is greater than the outside diameter of a male luer, and contains a solution for disinfecting the inner and outer surfaces of the male luer when inserted into the inner support structure. The silicone septum is secured to or against the inner support structure thereby forming a seal for maintaining the solution within the inner support structure. The silicone septum includes one or more slits that allow a male luer to be inserted through the septum into the inner support structure. The slits are configured such that when the male luer is inserted through the septum, the septum is secured around the outer surface of the male luer to inhibit the flow of solution out of the inner support structure.

FIG. 1A illustrates a perspective view of an exemplary disinfection cap 100 according to one or more embodiments of the invention. As shown, cap 100 includes an outer cylinder 101, an inner cylinder 102, and a septum 103 that is attached to the inner cylinder. Inner cylinder 102 can be configured to have a diameter that is larger than a standard female luer (i.e. larger than the outer diameter of the male luer) so that when the male luer is inserted into inner cylinder 102, the solution in inner cylinder 102 can freely flow into and around the male luer.

Although cap 100 is shown as being configured as a cylinder 101, other shapes can also be used such as a square, rectangle, oval, or other shaped outer surface. Also, cap 100 can have any reasonable length (e.g. to accommodate male luers of different lengths).

Figure 1B:
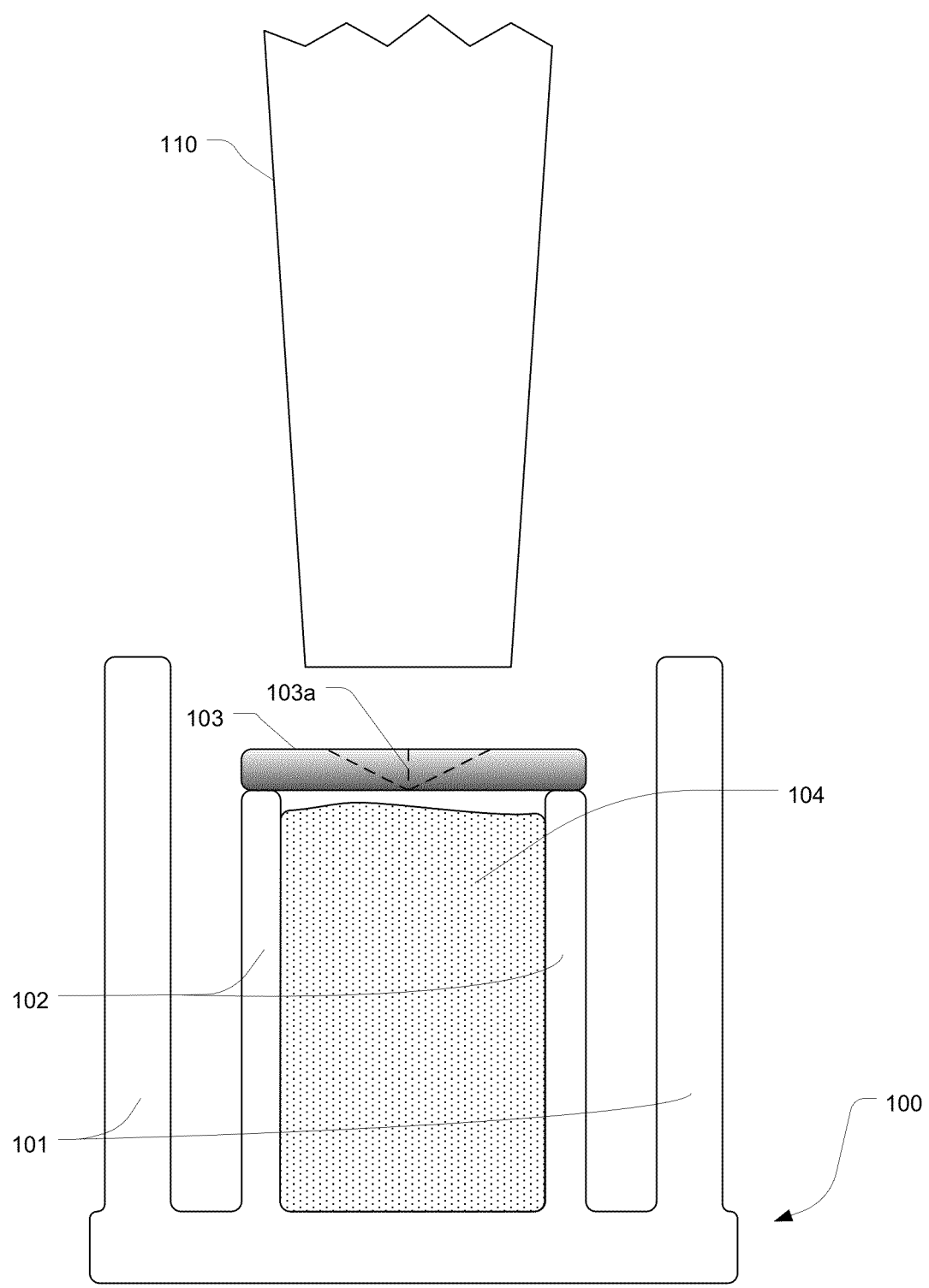
FIG. 1B illustrates a cross section view of the exemplary disinfection cap of FIG. 1A along with a male luer end of an infusion therapy device.

FIG. 1B illustrates a cross section view of cap 100 along with a male luer 110 of an infusion therapy device. As shown cap 100 includes a septum 103 that covers inner cylinder 102. Septum 103 can provide a seal over inner cylinder 102 that inhibits the evaporation of solution 104 contained in inner cylinder 102. Septum 103 can be made of any type of flexible material that deforms sufficiently to allow male luer 110 to be inserted through the septum while maintaining a substantial seal around male luer 110 to minimize the flow of solution 104 out of inner cylinder 102. In some embodiments, septum 103 can be made of silicone.

Septum 103 includes one or more slits or pierceable seams 103a that facilitate inserting male luer 110 through septum 103. In some embodiments, slits or seams 103a can extend out from the center of septum 103 to a distance that is less than the outer radius of male luer 110 so that a tight seal is formed between septum 103 and male luer 110 when the male luer is inserted through the septum.

Figure 1C:
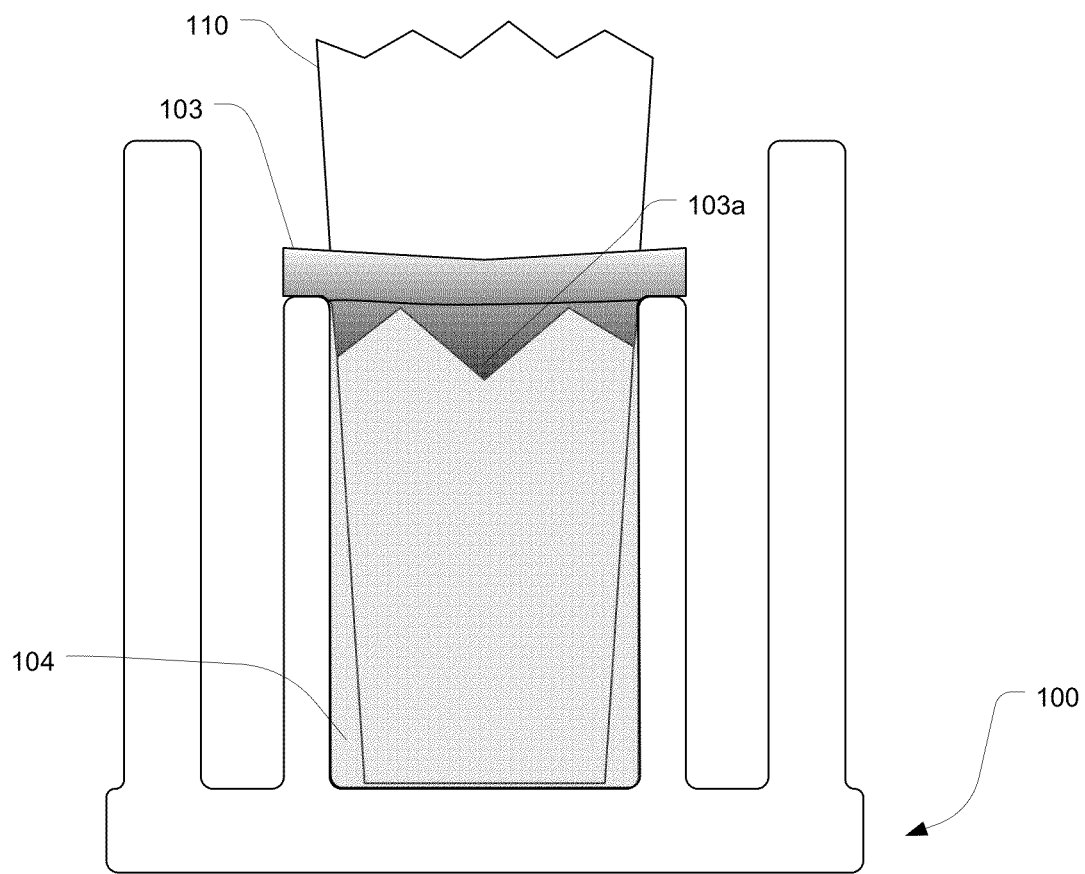
FIG. 1C illustrates that male luer end of the infusion therapy device shown in FIG. 1B has been inserted through the septum of the disinfection cap.

FIG. 1C illustrates that male luer 110 has been inserted through septum 103. As shown, slits or seams 103a have folded inwardly and are snug against the outer surface of male luer 110. In this manner, solution 104 can be better retained within inner cylinder 102, and evaporation can be limited. Solution 104 is thereby maintained in contact with the inner and outer surfaces of male luer 103 which increases the disinfectant effect on male luer 110.

Figure 2A:
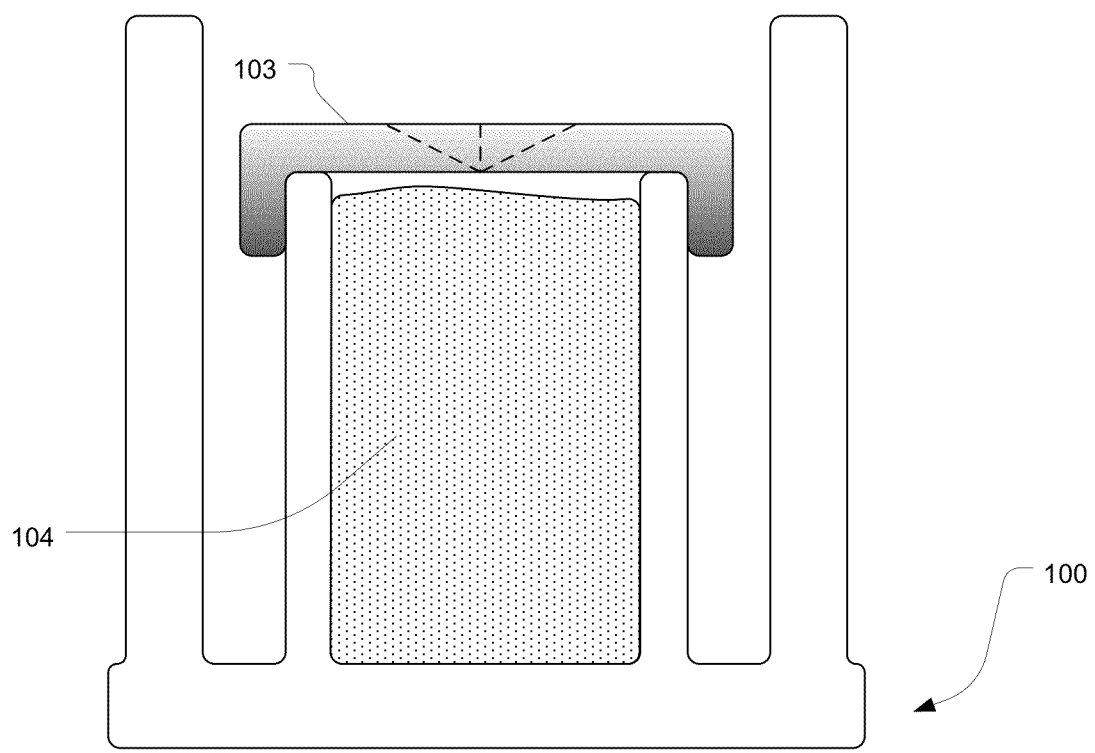
FIGS. 2A-2D illustrate various exemplary configurations of a septum.

FIG. 2A illustrates that septum 103 can be configured to wrap around the top end of inner cylinder 102. Because septum 103 can be made of a flexible elastic material, the septum can be attached to inner cylinder 102 in this manner without requiring any other means for securing the septum to the inner cylinder. Alternatively, additional means for securing the septum to inner cylinder can be used such as by gluing the septum to the inner cylinder.

Figure 2B:
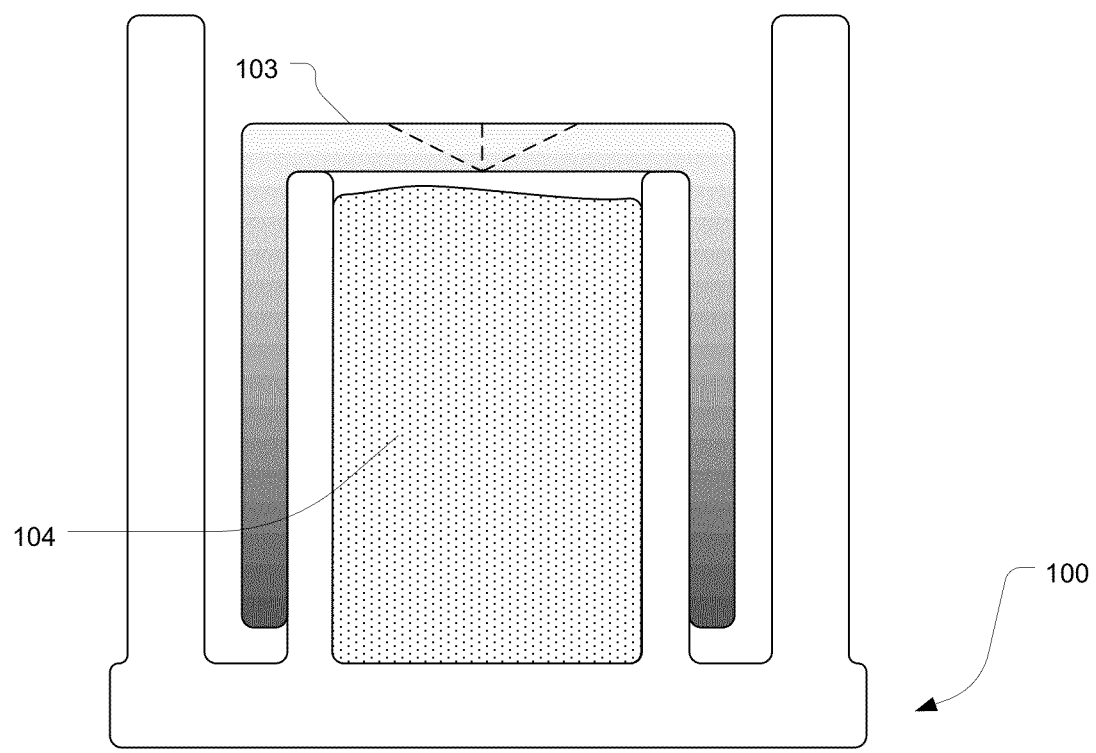

FIG. 2B illustrates a septum 103 similar to the septum shown in FIG. 2A. However, the extensions of septum 103 in FIG. 2B extend nearly the full length of inner cylinder 102. Accordingly, septum 103 can be configured with extensions of any length that wrap around a portion of inner cylinder 102.

Figure 2C:
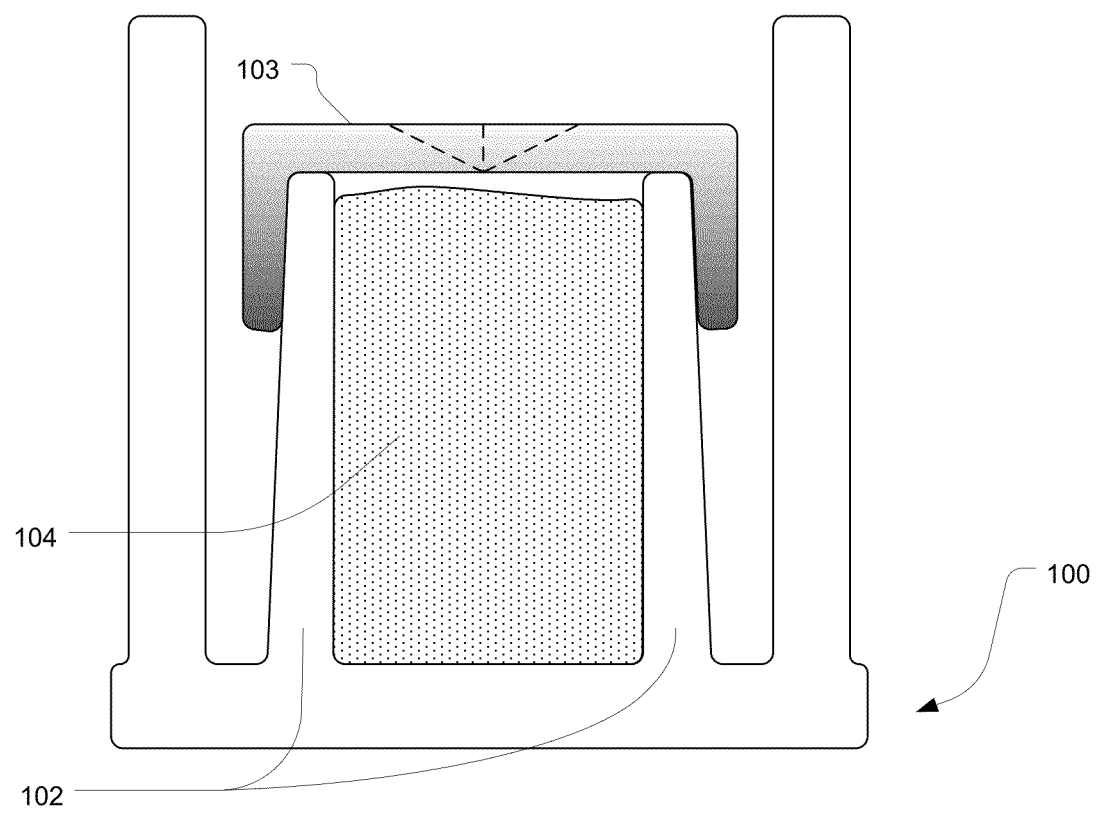

FIG. 2C illustrates an embodiment of cap 100 where inner cylinder 102 has a larger outer diameter at the bottom than at the top. A septum 103 with extensions of various lengths can be used in this embodiment. The increasing outer diameter of inner cylinder 102 can be used to better secure septum 103 to inner cylinder 102.

Although FIG. 2C shows a linear increase in the outer diameter of inner cylinder 102, in other embodiments, the outer diameter can be non-linear such as by including steps, ridges, or other non-linear increases to the outer diameter. Also, even though the outer surface of inner cylinder 102 is shown as and assumed to be circular, the outer surface can form another shape (e.g. an octagon or hexagon) or include any number of features (e.g. bumps, steps, or ridges) formed vertically on the outer surface.

Figure 2D:
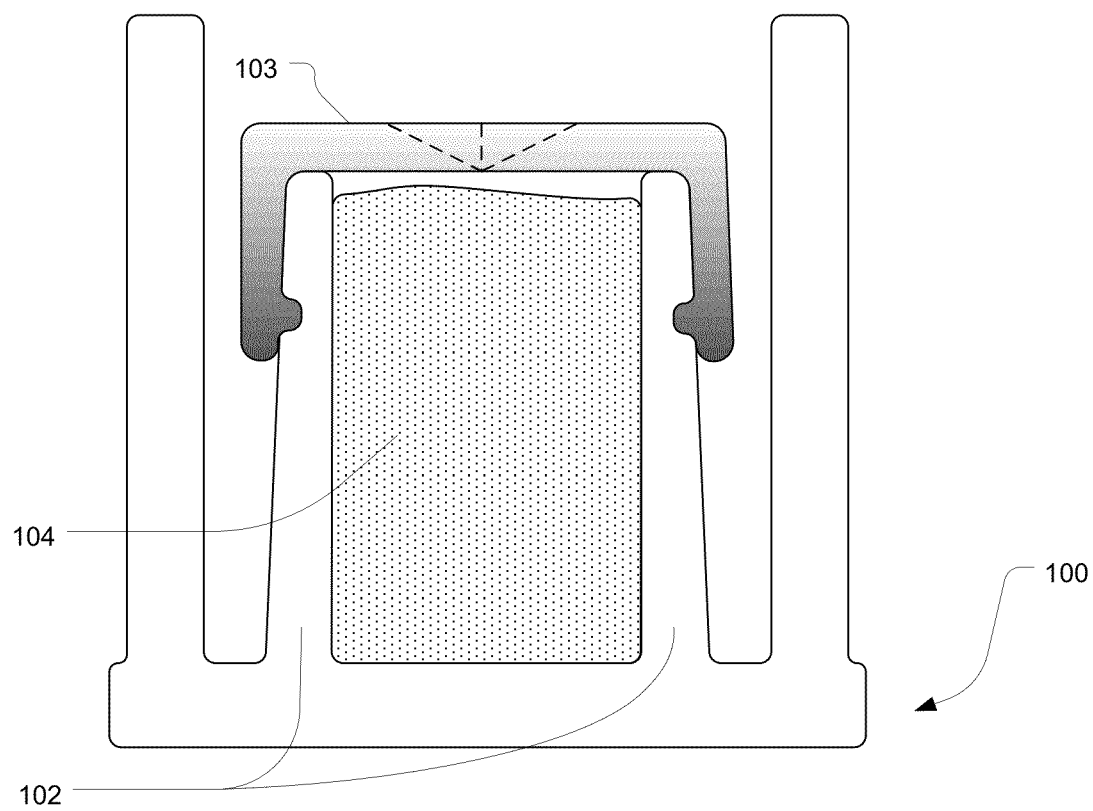

FIG. 2D illustrates an embodiment of cap 100 where inner cylinder 102 further comprises a groove or cut configured to receive a locking feature of septum 103. For example, in some embodiments the outer surface of inner cylinder 102 comprises an annular groove that is configured to receive an annular protrusion that is located on the inner surface of septum 103. The interaction between the locking feature of septum 103 and the groove or cut of inner cylinder 102 securely locks septum 103 to inner cylinder 102, as shown. Conversely, inner cylinder 102 may comprise an annular protrusion that is configured to be received by an annular groove located on the inner surface of septum 103.

Figure 3A:
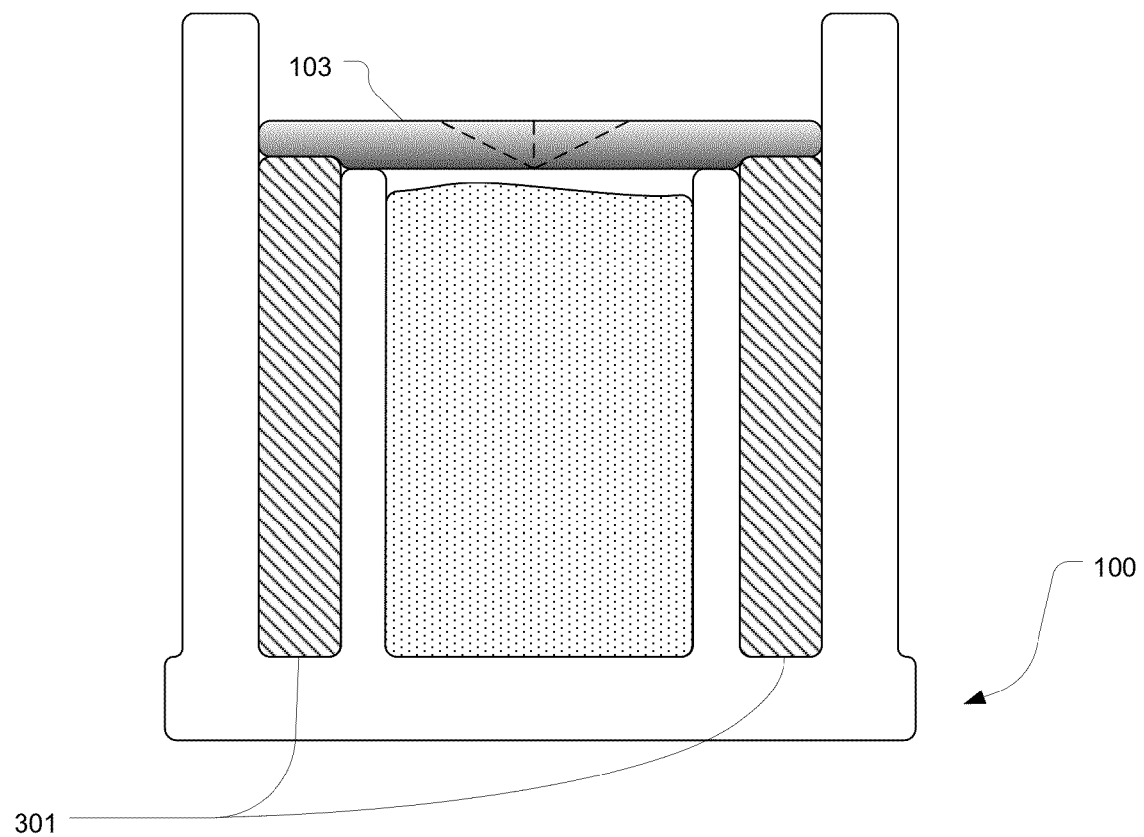
FIGS. 3A and 3B each illustrate an exemplary disinfection cap that employs a frame for securing the septum to the disinfection cap.

FIG. 3A illustrates an embodiment of cap 100 that employs a frame 301 for securing septum 103 to or against inner cylinder 102. Frame 301 can comprise a ring that is shaped to be inserted between outer cylinder 101 and inner cylinder 102. In some embodiments, frame 301 can be press fitted or glued to cap 100. Also, in some embodiments, septum 103 can be attached to frame 301 (e.g. by gluing) before frame 301 is attached to cap 100. Alternatively, septum 103 can be configured to attach to frame 301 after frame 301 has been attached to cap 100.

Figure 3B:
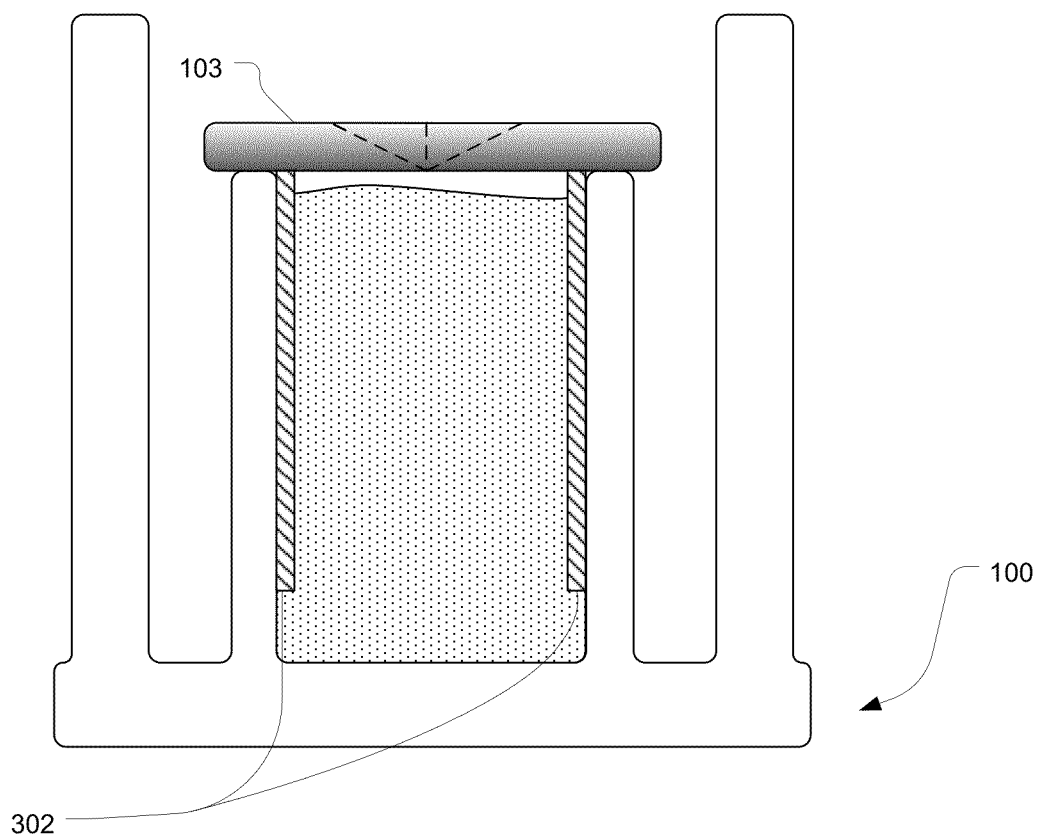

FIG. 3B illustrates an embodiment of cap 100 that employs a frame 302 for securing septum 103 to or against inner cylinder 102. Frame 302 can comprise a ring that has an outer diameter that is substantially the same as the inner diameter of inner cylinder 102. Like frame 301, frame 302 can be press fitted, glued, or otherwise attached to cap 100. When frame 302 is used, the inner diameter of inner cylinder 102 can be increased if necessary to ensure that the inner diameter of frame 302 is greater than the outer diameter of male luer 110. As with frame 301, septum 103 can be attached to frame 302 either before or after frame 302 has been attached to cap 100.

Figure 4A:
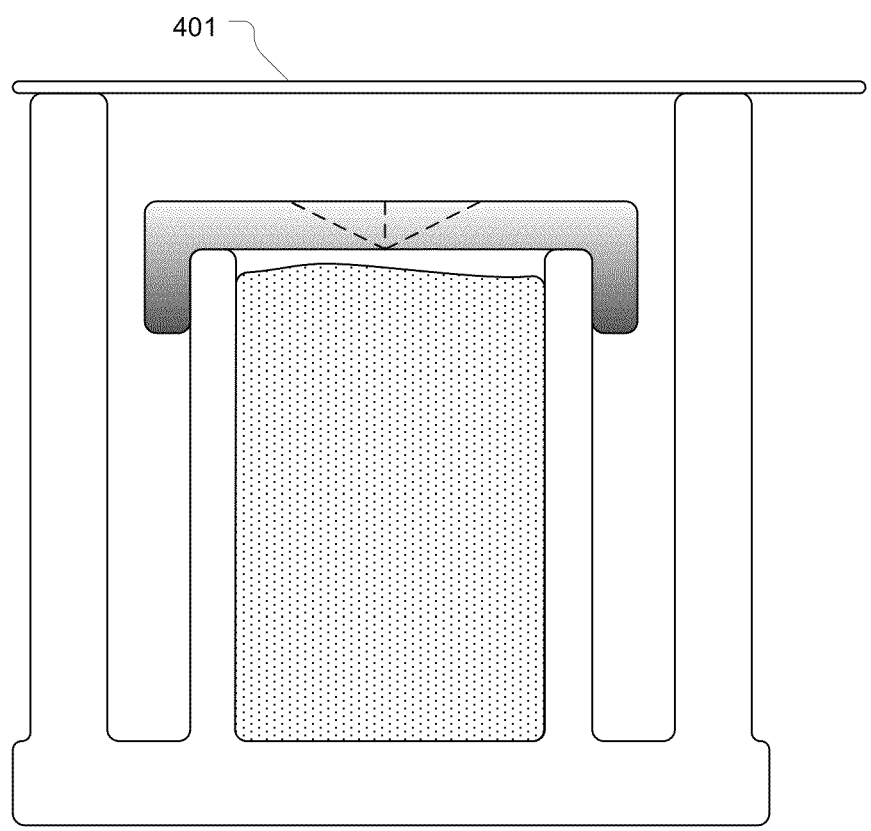
FIGS. 4A and 4B illustrate a foil seal that can be included on a disinfection cap.
Figure 4B:
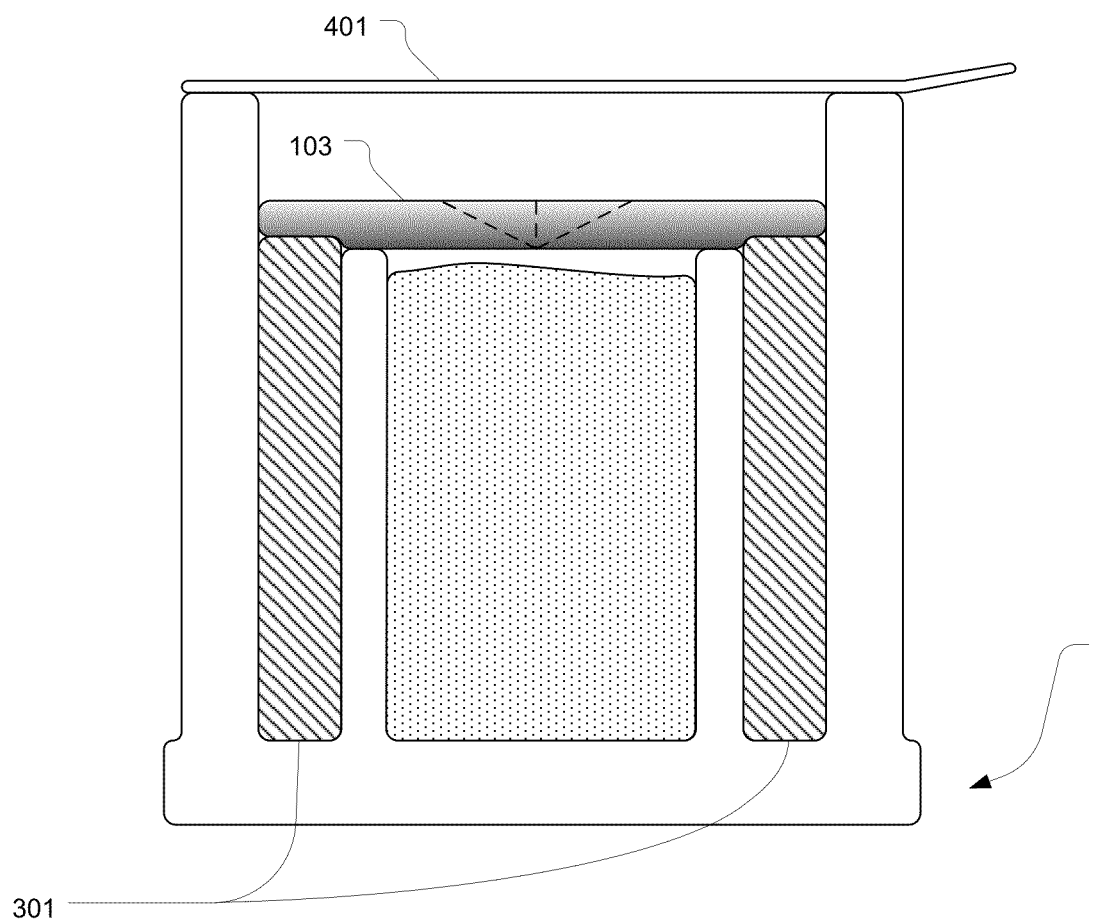

FIGS. 4A and 4B illustrate a seal 401 that can be included on cap 100. Seal 401 attaches to outer cylinder 101 to prevent evaporation of solution 104 from within inner cylinder 102 prior to seal 401 being removed. Seal 104 can be comprised of foil or any other material that can form a seal over cap 100. As shown, seal 401 can include one or more tabs to facilitate the removal of the seal.

Figure 5A:
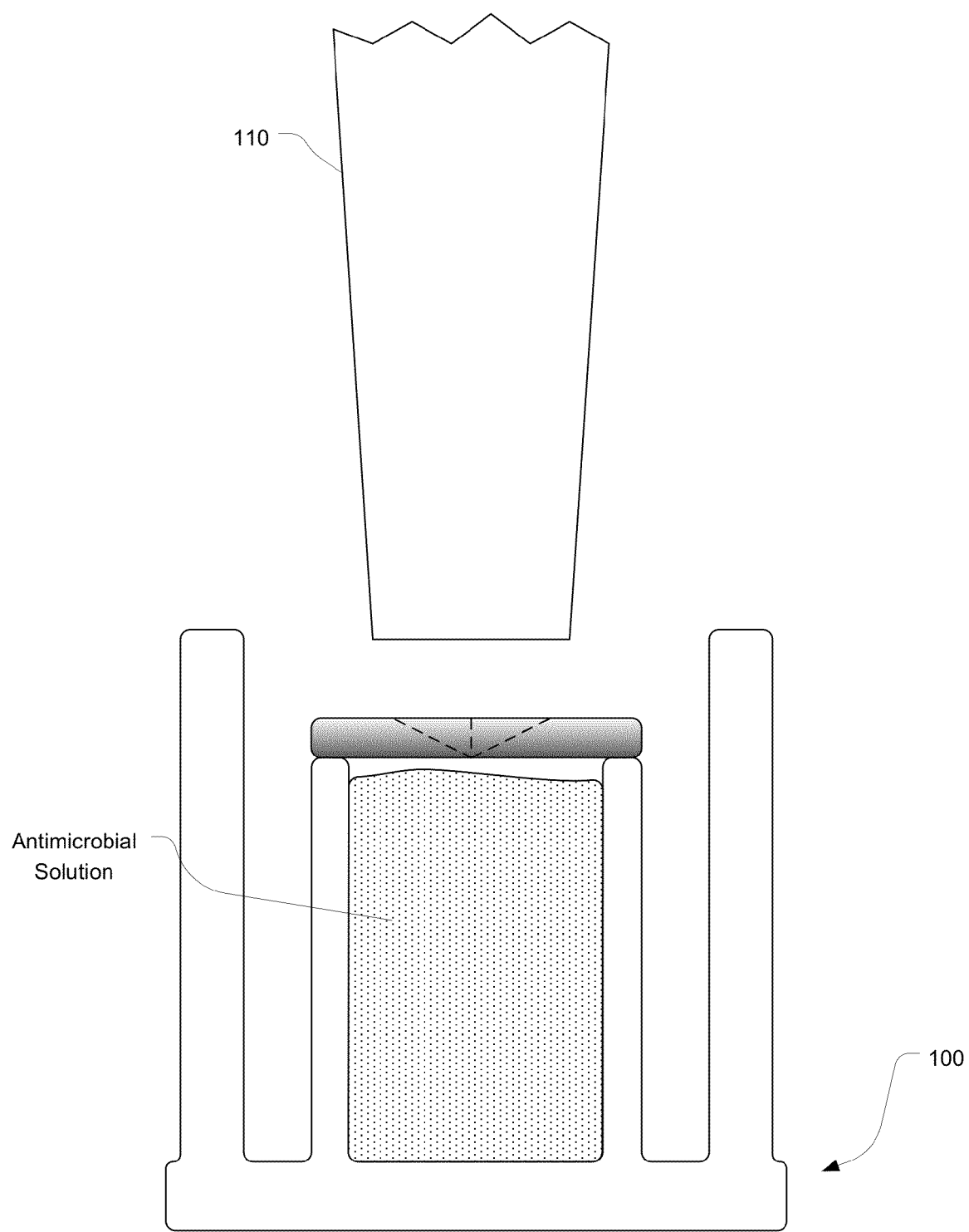
FIGS. 5A and 5B illustrate different ways in which an antimicrobial solution can be applied to a male luer end of an infusion therapy device.
Figure 5B:
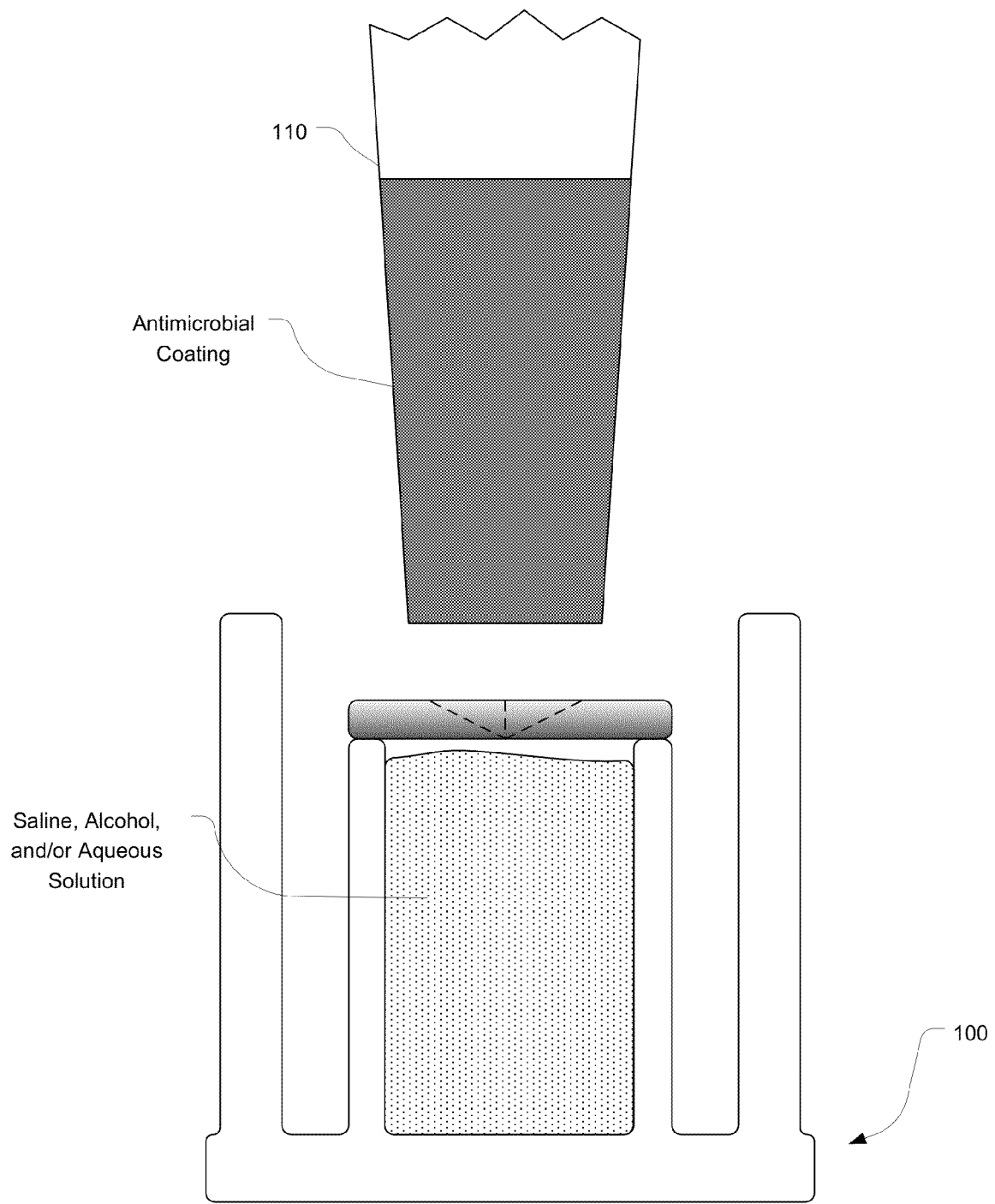

FIGS. 5A and 5B illustrate different ways in which an antimicrobial solution can be applied to male luer 110. In FIG. 5A, solution 104 comprises an antimicrobial solution. In such embodiments, male luer 110 does not need any antimicrobial coating. In contrast, in FIG. 5B, solution 104 comprises a saline, alcohol, or aqueous solution, and the outer surface of male luer 110 is coated with an antimicrobial coating. In such embodiments, the mixing of solution 104 with the antimicrobial coating disinfects both the outer and inner surfaces of male luer 110. Any type of solution that can disinfect a surface can be used as solution 104.

Figure 6:
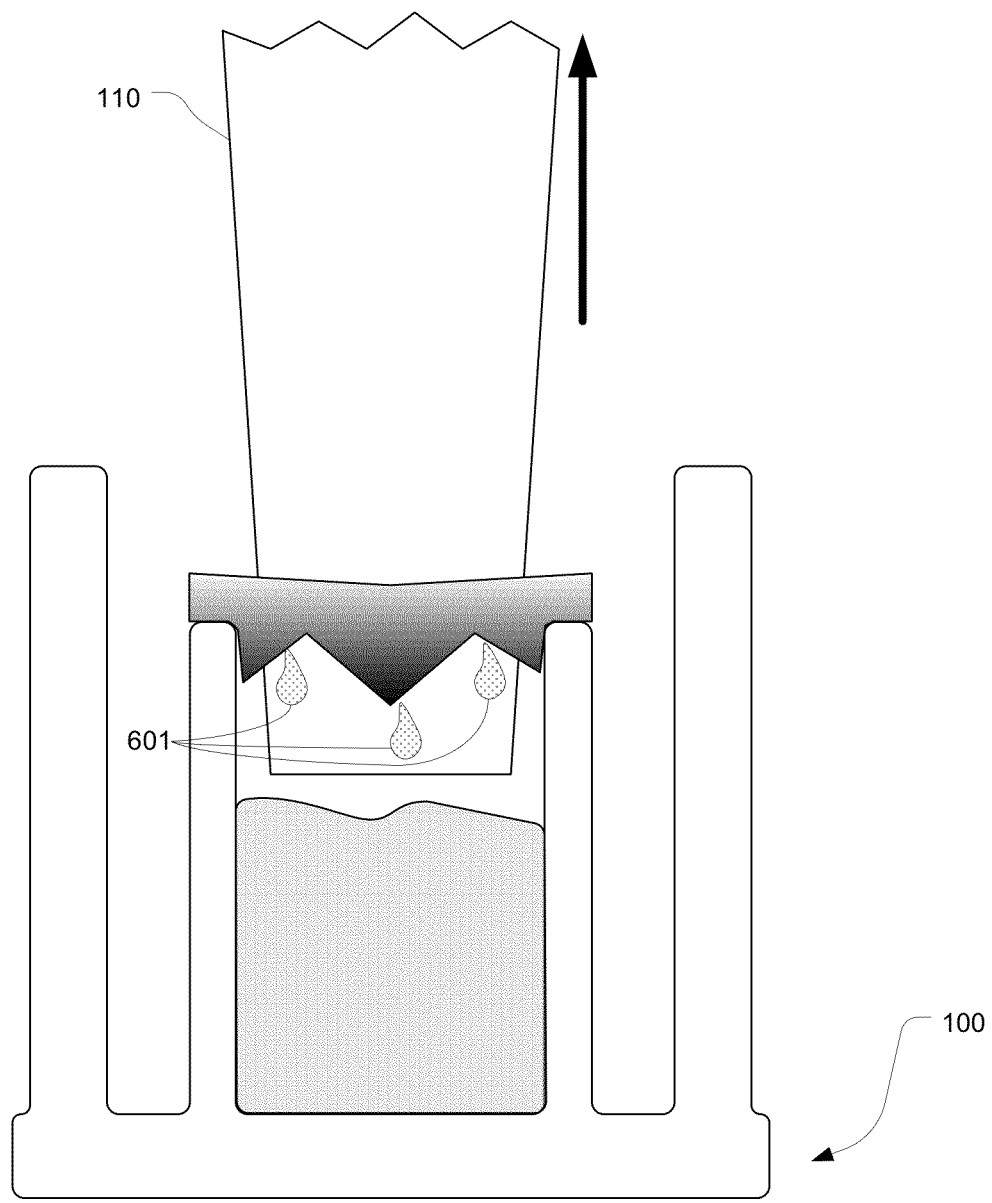
FIG. 6 illustrates how the septum can remove solution from the male luer as the male luer is pulled out through the septum.

FIG. 6 illustrates how the septum can remove solution from male luer 110 as the male luer is removed from septum 103. Because septum 103 is flexible and elastic, the septum maintains contact with the outer surface of male luer 110 as the male luer is removed. In this way, septum 103 in essence wipes the portions 601 of solution 104 that remain on the outer surface of male luer 104 as the male luer is removed. Removing solution 104 from male luer 110 is often desirable to minimize the amount of solution that can possibly enter the human body through the infusion therapy device.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A disinfection cap comprising:
   an outer support structure forming a first cavity;
   an inner support structure integrally formed with the outer support structure and positioned within the first cavity, the inner support structure having an inside diameter that is greater than the outside diameter of a male luer, the inner support structure forming a second cavity that contains a solution for disinfecting the inner and outer surfaces of the male luer when the male luer is inserted into the second cavity; and
   a septum attached to an outer top surface of the inner support structure thereby forming a seal for maintaining the solution within the second cavity, the septum being pierceable to allow a male luer to be inserted through the septum into the second cavity.

2. The cap of claim 1, wherein the outer support structure comprises a cylinder.

3. The cap of claim 1, wherein the inner support structure comprises a cylinder.

4. The cap of claim 1, wherein the solution comprises an antimicrobial solution.

5. The cap of claim 1, wherein the solution comprises a saline solution that mixes with an antimicrobial coating on the male luer.

6. The cap of claim 1, wherein the septum comprises silicone.

7. The cap of claim 1, wherein the septum includes one or more slits or seams that split when the male luer is inserted through the septum.

8. The cap of claim 7, wherein the one or more slits or seams have a radius from a center of the septum that is less than a radius of an outside diameter of the male luer such that the septum remains in contact with the outer surface of the male luer when the male luer is inserted through the septum.

9. The cap of claim 8, wherein the septum wipes solution from the outer surface of the male luer when the male luer is removed from the septum.

10. The cap of claim 1, further comprising:
    a seal that is attached to the outer support structure to form a seal over the first cavity.

11. The cap of claim 1, wherein the inner support structure has an outer diameter that increases from the top surface of the inner support structure towards a base of the inner support structure.

12. The cap of claim 1, wherein the septum includes an extension along an outer edge of the septum, wherein the extensions wraps around a portion of the inner support structure to attach the septum to the inner support structure.

13. The cap of claim 12, wherein the extension extends substantially to a base of the inner support structure.

14. A disinfection cap comprising:
    an outer support structure forming a first cavity;
    an inner support structure integrally formed with the outer support structure and positioned within the first cavity, the inner support structure having an inside diameter that is greater than the outside diameter of a male luer, the inner support structure forming a second cavity that contains a solution for disinfecting the inner and outer surfaces of the male luer when the male luer is inserted into the second cavity;
    a frame that is configured to be secured within the cap; and
    a septum attached to the frame such that when the frame is secured within the cap, the septum is secured to or against an outer top surface of the inner support structure thereby forming a seal over the second cavity for maintaining the solution within the second cavity, the septum being pierceable to allow a male luer to be inserted through the septum into the second cavity.

15. The cap of claim 14, wherein the frame is inserted between the outer and inner support structures.

16. The cap of claim 14, wherein the frame is inserted inside the second cavity.

17. The cap of claim 14, wherein the septum comprises silicone.

18. The cap of claim 14, wherein the septum includes one or more slits or seams that split when the male luer is inserted through the septum.

19. A disinfection cap comprising:

an outer support structure forming a first cavity;

an inner support structure integrally formed with the outer support structure and positioned within the first cavity, the inner support structure having an inside diameter that is greater than the outside diameter of a male luer, the inner support structure forming a second cavity that contains a solution for disinfecting the inner and outer surfaces of the male luer when inserted into the second cavity; and a silicone septum secured to or against an outer top surface of the inner support structure thereby forming a seal for maintaining the solution within the second cavity, the silicone septum including one or more slits that allow a male luer to be inserted through the septum into the second cavity, the slits being configured such that when the male luer is inserted through the septum, the septum is secured around the outer surface of the male luer to inhibit the flow of solution out of the second cavity.

20. The disinfection cap of claim 19, further comprising:

a frame to which the septum is attached, the frame being configured to be inserted into the cap such that the septum is positioned to be secured to or against the inner support structure.

* * * * *